United States Patent [19]
Saito et al.

[11] Patent Number: 5,158,770
[45] Date of Patent: Oct. 27, 1992

[54] AQUEOUS SOLUTION CONTAINING GINKGO LEAF EXTRACT

[75] Inventors: Yukihiro Saito, Ohmiya; Naomi Yoshida, Urawa; Seiichi Umeda, Iruma, all of Japan

[73] Assignees: Freund Industrial Co., Ltd.; Japan Greenwave Ltd., both of Tokyo, Japan

[21] Appl. No.: 634,393

[22] Filed: Dec. 27, 1990

[30] Foreign Application Priority Data

Dec. 29, 1989 [JP] Japan .................................. 1-344492
May 1, 1990 [JP] Japan .................................. 2-115514

[51] Int. Cl.$^5$ ..................... A61K 35/78; C08B 37/00; C13K 13/00
[52] U.S. Cl. ................... 424/195.1; 536/1.1; 127/29; 127/30; 127/33
[58] Field of Search ...................... 424/195.1; 536/1.1; 127/29, 30, 33

[56] References Cited

U.S. PATENT DOCUMENTS 4,465,667 8/1984 Byrod .................................. 424/156

*Primary Examiner*—Ronald W. Griffin
*Assistant Examiner*—Ralph G. Gitomer
*Attorney, Agent, or Firm*—Kane, Dalsimer, Sullivan, Kurucz, Levy, Eisele and Richard

[57] ABSTRACT

An aqueous solution containing a high concentration of ginkgo leaf extract having good preservability is prepared. The aqueous solution containing ginkgo leaf extract comprises at least 1 weight % of a hydrous organic solvent extract obtained from ginkgo leaf, and further disaccharide alcohols and/or trisaccharide alcohols, and/or organic compounds having a basic nitrogen atom in the molecule and a solubility in water at normal temperature of at least 10 g/100 ml.

6 Claims, No Drawings

AQUEOUS SOLUTION CONTAINING GINKGO LEAF EXTRACT

BACKGROUND OF THE INVENTION

1. Field of the Invention

The present invention relates to an aqueous solution of an extract obtained from ginkgo leaf (hereinafter referred to "ginkgo leaf extract") using a hydrous organic solvent.

2. Related Art Statement

Conventionally, in order to improve the circulation of blood throughout the brain, those medicines containing the ginkgo extract as an effective ingredient have widely been used in France or Germany. It is well known that the ginkgo extract provides useful pharmacological action of relaxing muscle of the blood vessel contracted by effect of stress and mental tension to reduce resistivity of peripheral artery and pharmacological actions of expanding the blood vessels, and accelerating the speed of blood circulation so that the volume of blood can eventually be increased. It is also known that the ginkgo extract effectively deals with peripheral blood vessel disease without causing side effect. By virtue of those advantageous reasons, the ginkgo extract is not only used for composing medicines, but also partly available in markets as health-promoting food. It is expected that ginkgo extract based drugs and foods will further come into wider use in the market.

On the other hand, the above ginkgo leaf extract is found still defective in that it is hardly soluble in water in spite of its solubility, for example, in organic solvent like alcohol. As a result, in order to allow consumers to internally take the ginkgo leaf extract without using alcohol, pharmacists are obliged to charge pulverized extract in solid capsules or mold it into tablets, thus limiting the application of this product to the preparation of solid medicines. However, those aged people and the sick find it easier to take liquid product than a solid one. Furthermore, liquid product can be more effectively absorbed into human body than the solid one, and thus, there is a growing demand among those concerned for an alcohol-free liquid product composed of the ginkgo leaf extract.

The present inventors have previously proposed a cooling beverage (soft drink) in which a ginkgo leaf extract is dissolved in water by using polydextrose (Japanese Patent Application No. 63-295372) as a means for solving the above problem.

However, since the above cooling beverage containing a ginkgo leaf extract is provided in the form of the ginkgo leaf extract previously diluted with water, a concentration of the ginkgo leaf extract necessarily becomes a dilute aqueous solution of 0.04 to 0.2% considering an appropriate intake amount of ginkgo leaf extract for adult (about 120 mg) and the appropriate diluted amount as a cooling beverage. Thus, there are inconveniences that many containers must be used and disposed, and purchase or storage is cumbersome for habitual use in a family.

In order to solve these inconveniences, a method employed is that a solution containing a high concentration of the ginkgo leaf extract is prepared and diluted with water when taking it. In fact, the ginkgo leaf extract has been sold in France or Germany in the form of a highly concentrated solution. However, this highly concentrated solution uses a high content of ethanol (to the extent of 30 to 50%) in order to dissolve the ginkgo leaf extract so that it is inappropriate for selling the solution to the general public as a health food. Also, in Japan, the ethanol content in non-alcoholic drinks is limited to 1% or less, so that such a high ethanol content solution cannot be marketed as non-alcoholic drinks.

On the other hand, there has been proposed a method in which the ginkgo leaf extract is dissolved in water with high concentration by using a sugar alcohol as a method of preparing high concentration solution of the ginkgo leaf extract without using an organic solvent such as ethanol. However, the present inventors have already pointed out (see Japanese Patent Application No. 63-295372) that when the method is applied to the above preparation of the ginkgo leaf extract cooling beverage, it becomes unsuitable for drink since an amount of the sugar alcohol becomes too excessive. When it is made in a high concentration solution, it is diluted with water when taking it so that there occurs no problem which is caused by excessive amount of the sugar alcohol.

However, according to the investigation by the present inventors, it was found that when a high concentration aqueous solution of the ginkgo leaf extract is to be prepared by using a sugar alcohol which is obtained by reduction of a monosaccharide (hereinafter referred to "monosaccharide alcohol") such as sorbitol, stable high concentration aqueous solution can not be obtained due to small stabilizing action of the monosaccharide alcohol. To the contrary, when a large amount of monosaccharide alcohols is added in order to obtain a stable high concentration aqueous solution, the monosaccharide alcohol is precipitated as crystals. Also, when a sugar alcohol obtained by reduction of oligosaccharide having a large molecular weight is used, it became clear that a high concentration aqueous solution which can be practically used can not be obtained since viscosity or transparency of the aqueous solution is lowered.

SUMMARY OF THE INVENTION

The inventors have achieved the present invention by studying methods of liquefying the ginkgo leaf extract and discovering means for fully solving those problems mentioned above.

The primary object of the present invention is to provide a technique of improving stability of an aqueous solution containing the ginkgo leaf extract in high concentration.

The above and further objects as well as novel features of the invention will more fully be apparent from the following detailed description of the preferred embodiments.

The invention provides an aqueous solution containing a ginkgo-leaf extract which comprises:

a ginkgo leaf extract; and, at least one sugar alcohols obtained by reduction of disaccharides (hereinafter referred to "disaccharide alcohols") and sugar alcohols obtained by reduction of trisaccharides (hereinafter referred to "trisaccharide alcohols"), and/or organic compounds having a basic nitrogen atom in the molecule and a solubility in water of at least 10 g/100 ml.

That is, the aqueous solution containing a ginkgo leaf extract of the present invention is:

(1) an aqueous solution containing a ginkgo leaf extract and at least one of disaccharide alcohols and trisaccharide alcohols, (2) an aqueous solution containing a ginkgo leaf extract and an organic compound having a basic nitrogen atom in the molecule and a solubility in water of at least 10 g/100 ml, and (3) an aqueous solution containing a ginkgo leaf extract, at least one of disaccharide alcohols and trisaccharide alcohols, and an organic compound having a basic nitrogen atom in the molecule and a solubility in water normal temperature is at least 10 g/100 ml.

In considering an appropriate ginkgo leaf extract intake amount per an adult and an appropriate diluted amount when taking it, a content of the ginkgo leaf extract in the ginkgo leaf extract-containing aqueous solution of the present invention is required to be at least 1% by weight in each case of the above (1) to (3).

The ginkgo leaf extract can be obtained according to the conventional method by extracting ginkgo leaves using a hydrous organic solvent such as hydrous methanol, hydrous ethanol, hydrous acetone, hydrous methyl ethyl ketone and then removing the solvent from the extract. The ginkgo leaf extract contains flavoglycoside, biflavone, ginkgoride as effective water-insoluble ingredients.

Maltitol, lactitol, reduced paratinose are exemplified as the disaccharide alcohol to be used in the present invention, among which maltitol is particularly preferred. Also, maltotriytol (also called as maltotriol) is exemplified as the trisaccharide alcohol. These di- and trisaccharide alcohols may be used singly or in combinations of two or more. Further, a small amount of monosaccharide alcohols produced by reducing a hydrolyzed product of starch, or sugar alcohols obtained by reduction of tetrasaccharides or larger polysaccharides can be mixed in the di- and trisaccharide alcohols used.

These sugar alcohols should be contained in the ginkgo leaf extract aqueous solution within the range of 30 to 75% by weight. If the content of the sugar alcohols is less than 30% by weight, it is difficult to dissolve ginkgo leaf extract in water with. To the contrary, if it exceeds 75% by weight, part of the sugar alcohols will likely be precipitated as crystals. From the viewpoints of dissolving the ginkgo leaf extract in water and preventing precipitation of the sugar alcohols, the trisaccharide alcohols are superior to the disaccharide alcohols. Accordingly, when the disaccharide alcohols and the trisaccharide alcohols are used combinedly, it is preferable that the trisaccharide alcohols are used with half or more amount in the total alcohols.

The ginkgo leaf extract-containing aqueous solution of the present invention may contain organic compounds having a basic nitrogen atom in the molecule and a solubility to water at normal temperature of at least 10 g/100 ml (hereinafter abbreviated to as "the organic compounds used in the present invention") in place of, or together with the above sugar alcohols (disaccharide alcohols and/or trisaccharide alcohols).

As the organic compounds used in the present invention, there may be exemplified, for example, amines such as urea, guanidine hydrochloride, ethanol amine, ethylenediamine, morpholine and derivatives thereof;

amino acids such as glycine, cysteine, threonine, arginine, lysine, histidine and derivatives thereof;

quaternary nitrogen-containing compounds such as alkyltrimethyl ammonium salt, alkyl pyridinium salt, betaine alkylacetate, betaine alkylimidazolium, pyridoxine hydrochloride (vitamin $B_6$), carnitine hydrochloride (vitamin $B_T$), thiamine hydrochloride (vitamin $B_1$);

acid amides such as formamide, dimethylformamide, nicotinic acid amide, calcium pantothenate, pantothenol.

Since primary use of the ginkgo leaf extract is in medicines (including external application) foods and drinks, particularly preferred organic compounds used in the aqueous solution containing ginkgo leaf extract of the present invention are amino acids, vitamins, urea, and physiologically acceptable surfactants among the above organic compounds used in the present invention.

The organic compounds used in the present invention have an action of improving storage stability of the aqueous solution containing the ginkgo leaf extract in a high concentration as in the above disaccharide alcohol or the trisaccharide alcohols. The minimum concentration of the organic compounds used in the aqueous solution containing ginkgo leaf extract of the present invention cannot be specified since it differs depending on the kinds, but usually it is 1% by weight or so. Also, a ratio of the organic compounds used in the present invention and the ginkgo leaf extract is that the former is preferably to be in excess of 10% by weight or more of the latter, and more preferably 20% by weight or more.

The aqueous solution containing ginkgo leaf extract comprising the ginkgo leaf extract and the organic compounds used in the present invention can be utilized for, in addition to medicines (for internal and external applications) foods and drinks, cosmetics.

When the aqueous solution containing the ginkgo leaf extract comprising the ginkgo leaf extract and the organic compound used in the present invention is used as a drink, it is preferable that the aforesaid disaccharide alcohols or the trisaccharide alcohols are added thereto. Addition of these sugar alcohols improves all the more the preservability of the aqueous solution containing ginkgo leaf extract comprising the ginkgo leaf extract and the organic compounds used in the present invention. Whereas the aqueous solution containing the ginkgo leaf extract comprising the ginkgo leaf extract and the sugar alcohols may sometimes precipitate the extract component with a lapse of time depending on the composition or storage conditions, its storage stability can be all the more improved by adding the organic compounds used in the present invention.

In the aqueous solution containing the ginkgo leaf extract the sugar alcohols and the organic compounds used in the present invention, the amounts added of the sugar alcohols and the organic compounds are reduced as compared with the aqueous solution containing the ginkgo leaf extract which does not contain either the sugar alcohol or the organic compound. For example, in the case of an aqueous solution to which 40% by weight or so of the sugar alcohols are added, the ginkgo leaf extract can be quickly dissolved at normal temperature even when the concentration of the organic compounds used in the present invention is about 0.02 to 0.1% by weight. Also, in the case of the aqueous solution containing the ginkgo leaf extract and the sugar alcohols but the organic compound used in the invention, it is difficult to dissolve the ginkgo leaf extract if the content of the sugar alcohols is less than 30% by weight. However, if it contains the organic compounds used in the present invention, the ginkgo leaf extract can be dissolved in water when the content of the sugar alcohols is at least 20% by weight.

In order to prepare the aqueous solution containing the ginkgo leaf extract and the sugar alcohols, it can be carried out by dissolving powder of the ginkgo leaf extract and disaccharide alcohols and/or trisaccharide alcohols in water under heating, and then diluting it with water.

The aqueous solution containing the ginkgo leaf extract and the organic compounds used in the present invention can be prepared by merely adding powder of the ginkgo leaf extract to an aqueous solution containing the organic compounds used in the present invention at normal temperature and stirring. Thus no specific operation such as heating is required. In this case, an easy and practical method is to add and dissolve the ginkgo leaf extract to concentrate aqueous solution of the organic compound used in the present invention which is substantially saturated, and then dilute the concentrate aqueous solution with water.

The aqueous solution containing the ginkgo leaf extract comprising the ginkgo leaf extract, the sugar alcohols and the organic compounds used in the present invention can be easily and practically prepared by adding the ginkgo leaf extract to concentrate aqueous solution of the organic compounds used in the present invention which is substantially saturated to dissolve the extract, thereafter the concentrate aqueous solution is diluted with water containing disaccharide alcohols or trisaccharide alcohols. In this case also, any specific operation such as heating is not required.

It is a surprising phenomenon that the ginkgo leaf extract which is insoluble in water at normal temperature is quickly dissolved in the aqueous solution of the organic compounds used in the present invention, which is considered to have less dissolving power. But it can be considered that some strong interaction between both components has been caused. For example, a glycoside of polyphenols which is a component of the ginkgo leaf extract and a basic nitrogen atom in the organic compounds used in the present invention probably have formed a molecular compound. The phenomenon that the ginkgo leaf extract is dissolved in an aqueous solution of a strong alkali (caustic alkali) has been known, but the above dissolution phenomenon found out by the present inventors is quite different from that in the dissolution mechanism.

In the aqueous solution containing the ginkgo leaf extract of the present invention thus prepared, there may be added various additives such as thickening agents (gum arabic), organic solvents which are acceptable as additives for foods (ethanol, propylene glycol), sweetenings (monosaccharide such as glucose, fructose; oligosaccharide such as sucrose, maltose; monosaccharide alcohol such as sorbitol, etc.; asperteme, stebia), colorants, perfumes, preservatives, nutrients. Addition of gum arabic or ethanol (not more than 1%) is particularly effective for improvement of storage stability.

The aqueous solution containing the ginkgo leaf extract of the present invention is excellent in stability in the state of aqueous solution of the ginkgo leaf extract, and can be stored stably for a long time without causing any precipitation. Particularly, those in a syrup state containing disaccharide alcohols and/or trisaccharide alcohols have a suitable viscosity and become a transparent aqueous solution which can be easily and quickly drinkable by diluting an apportioned small amount (1 to 20 ml or so) thereof with water (warm water, aqueous drinks such as juice may also be used).

DETAILED DESCRIPTION OF THE PREFERRED EMBODIMENTS

In the following, the present invention is described in more detail by referring to Examples.

EXAMPLE 1

A mixture composed of 2 g of dry powder of the ginkgo leaf extract, 115 g of Oligotose H-70 (trade name, produced by Mitsubishi Kasei Shokuhin Co., a reduced hydrolyzed starch product in liquid form which contains about 35 weight % of maltitol and 47 weight % of maltotriytol, both to the solid part, total solid being about 70% by weight) and 10 g of water was uniformly dispersed by using a homogenizer under heating to obtain a transparent syrup. This syrup had a viscosity of 200 cps at 20° C. and gave a transparent aqueous solution quickly when it was diluted with water. This syrup could be stored at 30° C. for a month and at 4° C. for 3 months stably.

EXAMPLE 2

A transparent syrup was obtained in the same manner as in Example 1 except for using 10 g of a 10 weight % aqueous gum arabic solution instead of 10 g of water. This syrup had a viscosity of 1500 cps at 20° C. and gave a transparent aqueous solution quickly when it was diluted with water. This syrup could be stored at 4° C. for 6 months and at 30° C. also for 6 months stably.

EXAMPLE 3

A mixture of 2 g of dry powder of the ginkgo-leaf extract, 115 g of Malti-syrup (trade name, produced by Towa Kasei Kogyo K. K., an aqueous solution containing 75 weight % of maltitol) and 10 g of water was uniformly dispersed by using a homogenizer to obtain a transparent syrup. This syrup had a viscosity of 1900 cps at 20° C. and gave a transparent aqueous solution quickly when it was diluted with water. This syrup could be stored at 30° C. for a month and at 4° C. for 2 months stably.

EXAMPLE 4

A transparent syrup was obtained in the same manner as in Example 3 except for using 40 g of Milktol (trade name, produced by Towa Kogyo K. K., lactitol), 40 g of Powder Malti (trade name, produced by Towa Kasei Kogyo K. K., maltitol) and 5 g of sorbitol, in place of 115 g of an aqueous solution containing 75 weight % of maltitol; and 40 g of a 10 weight % aqueous gum arabic solution in place of 10 g of water, respectively, and heating was effected. This syrup had a viscosity of 4200 cps at 20° C. and gave a transparent aqueous solution quickly when it was diluted with water. This syrup could be stored at 30° C. for a month and at 4° C. for 3 months stably.

EXAMPLE 5

A mixture of 1.5 g of dry powder of the ginkgo leaf extract, 80 g of Oligotose H-70, 30 g of sorbitol and 20 g of a 10 weight % aqueous gum arabic solution was uniformly dispersed by using a homogenizer under heating. This syrup had a viscosity of 350 cps at 20° C. and gave a transparent aqueous solution quickly when it was diluted with water. This syrup could be stored at 30° C. for a month and at 4° C. for 2 months stably.

COMPARATIVE EXAMPLE 1

A transparent syrup was obtained in the same manner as in Example 1 above except for using a 70 weight % aqueous sorbitol solution in place of Oligotose H-70. This syrup had a viscosity of 400 cps at 20° C. and became turbid when it was diluted with water. Also, when it is allowed to stand at 30° C., crystals of sorbitol were precipitated after one day.

COMPARATIVE EXAMPLE 2

A syrup was obtained in the same manner as in Example 1 except for using a 70 weight % aqueous reduced hydrolyzed starch product solution containing a sugar alcohol of tetramer or larger molecule, i.e. a sugar alcohol obtained by reduction of tetrasaccharide or larger polysaccharide, (such as maltotetraol, etc.) with a ratio of 60 weight % or more of the solid contents, in place of Oligotose H-70. This syrup was transparent immediately after the production. However, it became slightly turbid after 3 days whereby its commercial value was lowered, and a viscosity thereof at 20° C. became 8500 cps so that it can hardly be apportioned. Also, it became turbid when it was diluted with water.

COMPARATIVE EXAMPLE 3

A syrup having a viscosity of 105 cps at 20° C. was obtained in the same manner as in Example 5 except for using 60 g of Oligotose H-70 and 20 g of water in place of 80 g of Oligotose H-70. This syrup became turbid when diluted with water. Also, it became turbid when it was allowed to stand at 30° C. for 5 days.

COMPARATIVE EXAMPLE 4

A syrup was obtained in the same manner as in Example 4 except for changing an amount of the 10 weight % aqueous gum arabic solution from 10 g to 15 g. While this syrup had good fluidity at high temperature, it became an extremely viscous liquid without fluidity when cooled to 30° C. Also, it takes much time for diluting with water, and thus it is not a practically usable syrup.

EXAMPLE 6

(1) Solubility Test-1

Aqueous solutions were prepared by dissolving various organic compounds (No. 1 to No. 27) and an inorganic compound (No. 28) shown in Table 1 with an amount of each 5 g in 100 ml of water at 20° C. To each aqueous solution was added 10 g of dry powder of the ginkgo leaf extract and shaken for 10 minutes to observe the dissolution state. In the case of the organic compound having a solubility to water at 20° C. of 5 g/100 ml or less, a saturated solution was prepared and the ginkgo leaf extract was added twice the amount of the organic compound.

TABLE 1

| Organic compound | | Basic | Solubility (g/100 ml, | Dissolution |
|---|---|---|---|---|
| No. | Compound name | nitrogen | 20° C.) | state |
| 1 | Dimethylformamide | present | infinity | O |
| 2 | Monoethanol amine | present | infinity | O |
| 3 | Urea | present | 108 | O |
| 4 | Glycine | present | 22.5 | O |
| 5 | Cysteine hydrochloride | present | 110 | O |
| 6 | Threonine | present | 20 | O |
| 7 | Histidine | present | 42 | O |
| 8 | Lauryltrimethyl-ammonium chloride | present | 76 (at 0° C.) | O |
| 9 | Pyridoxine hydrochloride | present | 19 | O |
| 10 | Thiamine hydrochloride | present | 100 | O |
| 11 | Nicotinic acid amide | present | 50 | O |
| 12 | Calcium pantothenate | present | 19 | O |
| 13 | Valine | present | 8.5 | X |
| 14 | Methionine | present | 3.3 | X |
| 15 | Isoleucine | present | 3.8 | X |
| 16 | Taurine | present | 9 | X |
| 17 | Dicyandiamide | present | 3.2 | X |
| 18 | Nicotinic acid | present | 1.6 | X |
| 19 | Riboflavin | present | 0.01 | X |
| 20 | Glycerin | none | infinite | X |
| 21 | Acetic acid | none | infinite | X |
| 22 | Pyrogallol | none | 62.5 | X |
| 23 | Ascorbic acid | none | 22.4 | X |
| 24 | Citric acid | none | 59.4 | X |
| 25 | Sodium citrate | none | 67 | X |
| 26 | Sucrose | none | 66.4 | X |
| 27 | Sorbitol | none | 72 | X |
| 28 | Ammonium chloride (inoranic compound) | present | 27.1 | X |

Note)
Dissolution state:
O . . . dissolved to form a trans-parent aqueous solution
X . . . insoluble

TEST RESULTS

As can be clearly seen from Table 1, dry powder of the ginkgo leaf extract was completely dissolved in aqueous solutions of the organic compound (Nos. 1 to 12) having a basic nitrogen atom in the molecule and a solubility to water at 20° C. of 10 g/100 ml or more, but is insoluble in either of aqueous solutions of the organic compounds (Nos. 13 to 19) having a basic nitrogen atom in the molecule and a solubility to water at 20° C. of less than 10 g/100 ml, aqueous solutions of the organic compounds (Nos. 20 to 27) having no basic nitrogen atom in the molecule, or an aqueous solution of the inorganic compound (No. 28) having a basic nitrogen atom in the molecule and a solubility to water at 20° C. of 10 g/100 ml or more.

(2) Solubility Test-2

Aqueous solutions were prepared by dissolving 10 g of the organic compounds Nos. 1 to 12 shown in Table 1, respectively, in 100 ml of water at 20° C. To each of the aqueous solutions was added 20 g of dry powder of the ginkgo leaf extract and shaken for 10 minutes to observe the dissolution state after shaking. Each dry powder of the ginkgo leaf extract was completely dissolved in each of the aqueous solutions.

(3) Preservation Test

Aqueous solutions were prepared by dissolving 5 g of the organic compounds Nos. 1 to 12 shown in Table 1, respectively, in 100 ml of water at 20° C. To each of the aqueous solutions was added 10 g of the dry powder of the ginkgo leaf extract and shaken for 10 minutes to prepare transparent aqueous solutions containing the ginkgo leaf extract. These solutions were left to stand at room temperature for one month and then the state thereafter was observed. As the results, in either of the aqueous solutions containing the ginkgo leaf extract, no precipitation is generated and they are each stable aqueous solution.

EXAMPLE 7

An aqueous solution was prepared by dissolving 2 g of lysine hydrochloride in 5 g of water at 20° C. In the aqueous solution was dissolved 1 g of dry powder of the ginkgo leaf extract and further added 2 kg of maltitol syrup (a 75 weight % aqueous solution of maltitol), and then the mixture was made up to 5 liter by addition of water to prepare a ginkgo leaf extract-containing syrup. This syrup did not form any precipitation even when left to stand at room temperature for a month.

EXAMPLE 8

A ginkgo leaf extract-containing syrup was prepared in the same manner as in Example 7 except for using calcium pantothenate in place of lysine hydrochloride and using a sucrose syrup (a 65% by weight aqueous solution of sucrose) in place of a maltitol syrup. This syrup did not form any precipitation even when left to stand at room temperature for a month.

EXAMPLE 9

A ginkgo leaf extract-containing syrup was prepared in the same manner as in Example 7 except for using glycine in place of lysine hydrochloride and using 3 g of sodium alginate in place of 2 kg of a maltitol syrup. This syrup did not form any precipitation even when left to stand at room temperature for a month.

EXAMPLE 10

A ginkgo leaf extract-containing syrup was prepared in the same manner as in Example 9 except for using 2.5 g of decaglycerin monolaurate in place of 3 g of sodium alginate. This syrup did not form any precipitation even when left to stand at room temperature for 15 days.

EXAMPLE 11

An aqueous solution was prepared by dissolving 1 g of calcium pantothenate in 1 g of water at 20° C. In the aqueous solution was dissolved 1 g of dry powder of the ginkgo leaf extract and further added 13.3 g of a maltitol syrup (a 75 weight % aqueous solution of maltitol), the mixture was made up to 100 ml in total by adding water to prepare a ginkgo leaf extract-containing syrup. This syrup did not form any precipitation even when left to stand at room temperature for a month.

EXAMPLE 12

A transparent ginkgo leaf extract aqueous solution was prepared by dissolving 5 g of dry powder of the ginkgo leaf extract in 10 g (20° C.) of water saturated with urea. Even when this aqueous solution was diluted with water at 20° C. to 100-folds, no precipitation is formed.

COMPARATIVE EXAMPLE 5

After dissolving 1 g of dry powder of the ginkgo leaf extract in 100 ml (20° C.) of a 50 (v/v) % ethanol aqueous solution, water (20° C.) was added thereto to make the total amount of 5 liters. As the result, it became turbid with deposition of precipitates.

COMPARATIVE EXAMPLE 6

After dissolving 1 g of dry powder of the ginkgo leaf extract in 100 ml (20° C.) of a 50 (v/v) % ethanol aqueous solution and then further adding 2.5 g of decaglycerin monolaurate, water (20° C.) was added thereto to make the total amount of 5 liters. When the aqueous solution was left to stand at room temperature, it became turbid after 2 days with deposition of precipitates.

COMPARATIVE EXAMPLE 7

After dissolving 1 g of dry powder of the ginkgo leaf extract in 100 ml (20° C.) of a 50 (v/v) % ethanol aqueous solution and then adding 2 kg of sucrose syrup (a 65 weight % aqueous solution of sucrose), water (20° C.) was added thereto to make the total amount of 5 liters to prepare a transparent ginkgo leaf extract-containing syrup. When this syrup was left to stand at room temperature, it was turbid after 5 days also with deposition of precipitates.

COMPARATIVE EXAMPLE 8

To 1 g of water was added 1 g of dry powder of the ginkgo extract and the mixture was heated to 80° C. After the solution was uniformly dispersed with a homogenizer, 13.3 g of maltitol syrup (a 75 weight % of aqueous solution of maltitol) was added thereto and stirred. After cooling, water (20° C.) was added to make the total amount of 100 ml to prepare a slightly turbid ginkgo leaf extract-containing syrup. When this syrup was leaft to stand at room temperature, it was turbid after 3 days also with deposition of precipitates.

What is claimed is:

1. An aqueous solution which comprises;
   A. from 1 to 99 percent by weight of a hydrous organic solvent extract from ginkgo leaf, said solvent being selected from the group consisting of methanol, ethanol, acetone, and methyl ethyl ketone; and a compound selected from the group consisting of:
   B. from 20 to 75 percent by weight of the solution of alcohols selected from the group consisting of maltitol, lactitol, reduced paratinose and maltotriytol and
   C. from 0.02 to about 1 percent by weight of solution of organic compounds selected from the group consisting of urea, guanidine hydrochloride, ethanolamine, ethylenediamine, morpholine, glycine, cysteine, threonine, arginine, lysine, histidine, lauryltrimethylammonium salt, alkylpyridinium salt, betainealkylacetate, betainealkylimidazolium, pyridoxine hydrochloride, carnitine hydrochloride, thiamine hydrochloride, formamide, dimethylformamide, nicotinic acid amide, calcium pantothenate and pantothenol and has a solubility in water at room temperature of at least 10 g/100 ml.

2. The aqueous solution as set forth in claim 1, wherein, said alcohol is maltitol.

3. The aqueous solution as set forth in claim 1, wherein, said alcohol is maltotriytol.

4. The aqueous solution as set forth in claim 1, wherein,
   said solution comprises 30 to 75 percent by weight of component B.

5. The aqueous solution as set forth in claim 4, wherein, component B. selected is a mixture of a disaccharide alcohol and a trisaccharide alcohol and
   the content of said trisaccharide alcohols is ½ or more based on the total content of said disaccharide alcohols and said trisaccharide alcohols.

6. The aqueous solution as set forth in claim 1, wherein,
   the solution further comprises D. at least one member selected from the group consisting of gum arabic and ethanol in an amount less than 1 percent by weight of the solution.

* * * * *